US008298812B2

(12) United States Patent
Mueller et al.

(10) Patent No.: US 8,298,812 B2
(45) Date of Patent: *Oct. 30, 2012

(54) **USE OF *SACCHAROMYCES CEREVISIAE* ERG4 MUTANTS FOR EXPRESSING MAMMALIAN GLUCOSE TRANSPORTERS**

(75) Inventors: Guenter Mueller, Sulzbach am Taunus (DE); Silke Dlugai, Dusseldorf (DE); Doerthe Voss, Dusseldorf (DE); Eckhard Boles, Dusseldorf (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 32 days.

This patent is subject to a terminal disclaimer.

(21) Appl. No.: 12/614,710

(22) Filed: Nov. 9, 2009

(65) Prior Publication Data
US 2010/0203617 A1    Aug. 12, 2010

Related U.S. Application Data

(63) Continuation of application No. 11/775,384, filed on Jul. 10, 2007, now Pat. No. 7,615,360, which is a continuation of application No. 10/659,234, filed on Sep. 10, 2003, now Pat. No. 7,244,821.

(60) Provisional application No. 60/455,340, filed on Mar. 17, 2003.

(30) Foreign Application Priority Data

Sep. 14, 2002   (DE) ................. 102 42 763

(51) Int. Cl.
C12N 1/16       (2006.01)
C12N 9/02       (2006.01)
C12P 7/64       (2006.01)
C07H 21/04      (2006.01)

(52) U.S. Cl. ............... 435/254.2; 435/254.11; 435/134; 435/189; 536/23.1; 536/23.2; 536/23.5

(58) Field of Classification Search .................. None
See application file for complete search history.

(56) References Cited

U.S. PATENT DOCUMENTS

| | | | |
|---|---|---|---|
| 6,346,374 | B1 | 2/2002 | Tartaglia |
| 7,244,821 | B2 * | 7/2007 | Mueller et al. ............. 530/350 |
| 2003/0166258 | A1 * | 9/2003 | Muller et al. ............ 435/254.21 |
| 2004/0101848 | A1 | 5/2004 | Ward |
| 2005/0147987 | A1 | 7/2005 | Venter et al. |

FOREIGN PATENT DOCUMENTS

WO   WO 00/75188   12/2000
WO   WO 02/064784   8/2002

OTHER PUBLICATIONS

Burns Nancy et al., Large-Scale Analysis of Gene Expression, Protein Localization, and Gene Disruption in *Saccharomyces cerevisiae*, Genes & Development, (1994), vol. 8, pp. 1087-1105.

Buse, John B. et al., Human GLUT4/Muscle-Fat Glucose-Transporter Gene, Diabetes, (1992), vol. 41, pp. 1436-1445.
Fukumoto et al., Cloning and Characterization of the Major Insulin-responsive Glucose Transporter Expressed in Human Skeletal Muscle and Other Insulin-responsive Tissues, Journal of Bio. Chem., vol. 264, No. 15, May 15, 1989, pp. 7776-7779.
Wieczorke Roman et al., Concurrent Knock-Out of At Least 20 Transporter Genes Is Required to Block Uptake of Hexoses in *Saccharomyces cerevisiae*, FEBS Letter, (1999), vol. 464, pp. 123-128.
Wieczorke, R., Molekulargenetische und physiologische Untersuchungen zur Funktion von FGY1 bei der heterologen Expression von Glukosetransportern in der Hefe *Saccharomyces cerevisiae*. Thesis, Heinrich-Heine-Universität Düsseldorf, 2001.
Asano et al., The Role of N-Glycosylation of GLUT1 for Glucose Transport Activity, J. of Biol. Chem., vol. 286, No. 36, Dec. 15, 1991, pp. 24632-24636.
Birnbaum et al., Cloning and Characterization of a cDNA encoding the rat brain glucose-transporter protein, Proc. Natl. Acad Sci, USA, vol. 83, Aug. 1986, pp. 5784-5788.
Birnbaum et al., Gen Bank Acc. No. P11167, Cloning and characterization of cDNA enclocling the rat brain glucose-transporter protein, PNAS, vol. 83, No. 16, 1986, pp. 5784-5788.
Birnbaum et al., Gen Bank Acc. No. M13979, Cloning and characterization of a cDNA encoding the rat brain glucose-transporter protein, PNAS, vol. 83, No. 26, 1986, pp. 5784-5788.
Boles et al., A rapid and highly efficient method for PCR-based site-directed mutagenesis using only one new primer, Curr. Gent., vol. 28, 1995, pp. 197-198.
Doege et al., GenBank Acc. No. Y17803, Activity and genomic organization of human glucose transporter 9 (GLUT9), a novel member of the familty of sugar-transport facilitators predominantly expressed in brain and leucocytes. Biochem J. 350 Pt. 3, 2000, 771-776.
Fukomoto et al., Gen Bank Acc. No. M20653, Characterization and expression of human HepG2/erythrocyte glucose-transporter gene, Diabetes, vol. 37, No. 5, 1988, pp. 657-661.
Fukomoto et al., Gen Bank Acc. No. P14672, Cloning and characterization of the major insulin-responsive glucose transporter expressed in human skeletal msucle and other insulin-responsive tissues, J. Biol. Chem., vol. 264, No. 14, 1989, pp. 7776-7779.
Fukomoto et al., Gen Bank Acc. No. M20747, Cloning and characterization of the major insulin-responsive glucose transporter expressed in human skeletal muscle and other insultin-responsive tissues, J. Biol. Chem, 274, No. 14, 1989, pp. 7776-7779.
Iwashima et al., Gen Bank Acc. No. M23382, Variable region (V delta) gene segment most frequently utilized in adult thymocytes is a 3' of the constatn (C delta) region, PNAS, vol. 85, No. 21, 1988. pp. 8161-8165.

(Continued)

Primary Examiner — Robert Mondesi
Assistant Examiner — Iqbal H Chowdhury
(74) Attorney, Agent, or Firm — Nicole Parsons

(57) ABSTRACT

The invention relates to yeast strains in which a human GLUT4 transport or a human GLUT1 transporter can be functionally expressed and to particular GLUT4 transport proteins which can be functionally expressed particularly readily in yeast strains.

3 Claims, No Drawings

OTHER PUBLICATIONS

James et al., Gen Bank Acc. No. P19357, Molecular cloning and characterization of an insulin-regulatable glucose transporter, Nature, vol. 338. 1989. pp. 83-87.

Kaestner et al., Can Bank Acc. No. M23384, Sequence, tissue distribution and differential expression of mRNA for a putative insulin-responsive glucose transporter in mouse 3T3-L1 adipocytes, PNAS, USA 86 (9) 1989, pp. 3150-3154.

Kaestner et al., Gen Bank Acc. No. P14142, Sequences, tissue distribution, and differential expression of mRNA for a putative insulin-responsive glucose transporter in mouse 3T3-L1 adipocytes, PNAS. vol. 86, No. 9, 1989, pp. 3150-3154.

Kaestner et al., Gen Bank Acc. No. P17809, Sequence, tissue distribution, and differential expression of mRNA for a p putative insulin-responsive glucose transporter in mouse 3T3-L1 adipocytes, PNAS, vol. 86, No. 9, 1989, pp. 3150-3154.

Kasahara et al., Characterization of rat Glut4 glucose transporter expressed in the yeast *Saccharomyces cerevisiae*: comparison with Glut1 glucose transporter, Biochimica et Biophysica Acta, vol. 1324, 1997, pp. 111-119.

Kasahara et al., Expression of the rat GLUT1 glucose transporter in the yeat *Saccharomyces cerevisiae*, Biochem. J. vol. 315, 1996, pp. 177-182.

Kasahara et al., Gen Bank Acc. No. D28561. Characterization of rat Glut 4 glucose transporter expressed in the yat *Saccharomyces cerevisiae*: comparison with Glut1 glucose, Biochim. Biophys. Acta 1324, 1997, pp. 111-119.

Kasahara et al., Studies of the Glut Familty Transporters: Use of the Yeast Expression System, Int. Symp. Kyushu Univ. 1997, pp. 201-212.

Kasahara et al., Tryptophan 388 in Putative Transmembrane Segment 10 of the Rat Glucose Transporter Glut1 Is Essential for Glucose Transport, J. of Biol. Chem., vol. 273, No. 44, Oct. 30, 1998, pp. 29113-29117.

Kruckberg et al., The HXT2 Gene of *Saccharomyces cerevisiae* Is Required for High-Affinity Glucose Transport, Molecular and Cellular Biology, vol. 10, No. 11, Nov. 1990, pp, 5903-5913.

McDonough et al., Mutations in erg4 affect the sensitivity of *Saccharomyces cerevisiae* to medium-chain fatty acids, Biochimica et Biophysica Acta, 1581, 2002, pp. 109-118.

Mueckler et al., Gen Bank Acc. No. P11166, Sequence and structure of a human glucose transporter, Science, vol. 229. 1985, pp. 941-945.

Ngo et al., Computational Complexity, Protein Structure Prediction, and the Levinthal Paradox, The Protein Folding Problem and Tertiary Structure Prediction, 1994, Merz et al., (Birkhauser, Boston, MA, 1994, pp. 433 and 492-495.

Voss, D., Molekulargenetische Untersuchungen zur Funktion von FGY1-Gens bei der Expression heterologer Glukosetransporter in *Saccharomyces cerevisiae*, diploma thesis, Heinrich-Heine-Universität Düsseidorf, Dec. 2001.

Wieczorke et al., Characterisation of Mammalian GLUT Glucose Transporters in a Heterologous Yeast Expression System, Cell Physiol. Biochem. vol. 13, 2003, pp. 123-134.

U.S. Appl. No. 10/067,449 Non-Final Office Action mailed May 18, 2004.

U.S. Appl. No. 10/067,449 Final Office Action mailed Jan. 25, 2005.

* cited by examiner

SEQUENCE LISTING

```
<160> NUMBER OF SEQ ID NOS: 3

<210> SEQ ID NO 1
<211> LENGTH: 1530
<212> TYPE: DNA
<213> ORGANISM: Homo sapiens

<400> SEQUENCE: 1
atgccgtcgg gcttccaaca gataggctcc gaagatgggg aaccccctca gcagcgagtg      60
actgggaccc tggtccttgc tgtgttctct gcggtgcttg gctccctgca gtttgggtac     120
aacattgggg tcatcaatgc ccctcagaag gtgattgaac agagctacaa tgagacgtgg     180
ctggggaggc aggggcctga gggacccagc tccatccctc caggcaccct caccacccct     240
tgggccctct ccatggccat cttttccgtg ggcggcatga tttcctcctt cctcattggt     300
atcatctctc agtggcttgg aaggaaaagg gccatgctgg tcaacaatgt cctggcggtg     360 ctgggggggca gcctcatggg cctggccaac gctgctgcct cctatgaaat gctcatcctt     420
ggacgattcc tcattggcgc ctactcaggg ctgacatcag gctggtgcc catgtacgtg     480 ggggagattg ctcccactca cctgcgggcc gccctgggga cgctcaacca actggccatt     540
gttatcggca ttctgatcgc ccaggtgctg ggcttggagt ccctcctggg cactgccagc     600
ctgtggccac tgctcctggg cctcacagtg ctacctgccc cctgcagct ggtcctgctg     660 cccttctgtc ccgagagccc ccgctacctc tacatcatcc agaatctcga ggggcctgcc     720
agaaagagtc tgaagcgcct gacaggctgg gccgatgttt ctggagtgct ggctgagctg     780
aaggatgaga gcggaagct ggagcgtgag cggccactgt ccctgctcca gctcctgggc     840
agccgtaccc accggcagcc cctgatcatt gcggtcgtgc tgcagctgag ccagcagctc     900
tctggcatca atgctgtttt ctattattcg accagcatct tcgagacagc aggggtaggc     960
cagcctgcct atgccaccat aggagctggt gtggtcaaca cagtcttcac cttggtctcg    1020
gtgttgttgg tggagcgggc gggggcgccgg acgctccatc tcctgggcct ggcgggcatg    1080
tgtggctgtg ccatcctgat gactgtggct ctgctcctgc tggagcgagt tccagccatg    1140
agctacgtct ccattgtggc catctttggc ttcgtggcat tttttgagat tggccctggc    1200
cccattcctt ggtcatcgt ggccgagctc ttcagccagg accccgccc ggcagccatg    1260 gctgtggctg gtttctccaa ctggacgagc aacttcatca ttggcatggg tttccagtat    1320 gttgcgagg ctatggggcc ctacgtcttc cttctatttg cggtcctcct gctgggcttc    1380
ttcatcttca ccttcttaag agtacctgaa actcgaggcc ggacgtttga ccagatctca    1440
gctgccttcc accggacacc ctctcttta gagcaggagg tgaaacccag cacagaactt    1500
```
gagtatttag ggccagatga gaacgactga                                         1530

<210> SEQ ID NO 2
<211> LENGTH: 509
<212> TYPE: PRT
<213> ORGANISM: Homo sapiens

<400> SEQUENCE: 2

Met Pro Ser Gly Phe Gln Gln Ile Gly Ser Glu Asp Gly Glu Pro Pro
1               5                   10                  15

Gln Gln Arg Val Thr Gly Thr Leu Val Leu Ala Val Phe Ser Ala Val
                20                  25                  30

Leu Gly Ser Leu Gln Phe Gly Tyr Asn Ile Gly Val Ile Asn Ala Pro
            35                  40                  45

Gln Lys Val Ile Glu Gln Ser Tyr Asn Glu Thr Trp Leu Gly Arg Gln
    50                  55                  60

Gly Pro Glu Gly Pro Ser Ser Ile Pro Pro Gly Thr Leu Thr Thr Leu
65                  70                  75                  80

Trp Ala Leu Ser Met Ala Ile Phe Ser Val Gly Gly Met Ile Ser Ser
                85                  90                  95

Phe Leu Ile Gly Ile Ile Ser Gln Trp Leu Gly Arg Lys Arg Ala Met
                100                 105                 110

Leu Val Asn Asn Val Leu Ala Val Leu Gly Gly Ser Leu Met Gly Leu
            115                 120                 125

Ala Asn Ala Ala Ala Ser Tyr Glu Met Leu Ile Leu Gly Arg Phe Leu
    130                 135                 140

Ile Gly Ala Tyr Ser Gly Leu Thr Ser Gly Leu Val Pro Met Tyr Val
145                 150                 155                 160

Gly Glu Ile Ala Pro Thr His Leu Arg Gly Ala Leu Gly Thr Leu Asn
                165                 170                 175

Gln Leu Ala Ile Val Ile Gly Ile Leu Ile Ala Gln Val Leu Gly Leu
            180                 185                 190

Glu Ser Leu Leu Gly Thr Ala Ser Leu Trp Pro Leu Leu Leu Gly Leu
    195                 200                 205

Thr Val Leu Pro Ala Leu Leu Gln Leu Val Leu Leu Pro Phe Cys Pro
210                 215                 220

Glu Ser Pro Arg Tyr Leu Tyr Ile Ile Gln Asn Leu Glu Gly Pro Ala
225                 230                 235                 240

Arg Lys Ser Leu Lys Arg Leu Thr Gly Trp Ala Asp Val Ser Gly Val
                245                 250                 255

Leu Ala Glu Leu Lys Asp Glu Lys Arg Lys Leu Glu Arg Glu Arg Pro
            260                 265                 270

Leu Ser Leu Leu Gln Leu Leu Gly Ser Arg Thr His Arg Gln Pro Leu
    275                 280                 285

Ile Ile Ala Val Val Leu Gln Leu Ser Gln Gln Leu Ser Gly Ile Asn
290                 295                 300

Ala Val Phe Tyr Tyr Ser Thr Ser Ile Phe Glu Thr Ala Gly Val Gly
305                 310                 315                 320

Gln Pro Ala Tyr Ala Thr Ile Gly Ala Gly Val Val Asn Thr Val Phe
                325                 330                 335

Thr Leu Val Ser Val Leu Val Glu Arg Ala Gly Arg Arg Thr Leu
            340                 345                 350

His Leu Leu Gly Leu Ala Gly Met Cys Gly Cys Ala Ile Leu Met Thr
    355                 360                 365

Val Ala Leu Leu Leu Leu Glu Arg Val Pro Ala Met Ser Tyr Val Ser

```
            370             375             380
Ile Val Ala Ile Phe Gly Phe Val Ala Phe Glu Ile Gly Pro Gly
385                 390                 395                 400

Pro Ile Pro Trp Phe Ile Val Ala Glu Leu Phe Ser Gln Gly Pro Arg
                405                 410                 415

Pro Ala Ala Met Ala Val Ala Gly Phe Ser Asn Trp Thr Ser Asn Phe
                420                 425                 430

Ile Ile Gly Met Gly Phe Gln Tyr Val Ala Glu Ala Met Gly Pro Tyr
                435                 440                 445

Val Phe Leu Leu Phe Ala Val Leu Leu Leu Gly Phe Phe Ile Phe Thr
450                 455                 460

Phe Leu Arg Val Pro Glu Thr Arg Gly Arg Thr Phe Asp Gln Ile Ser
465                 470                 475                 480

Ala Ala Phe His Arg Thr Pro Ser Leu Leu Glu Gln Glu Val Lys Pro
                485                 490                 495

Ser Thr Glu Leu Glu Tyr Leu Gly Pro Asp Glu Asn Asp
                500                 505

<210> SEQ ID NO 3
<211> LENGTH: 7809
<212> TYPE: DNA
<213> ORGANISM: Saccharomyces cerevisiae

<400> SEQUENCE: 3
cgtaggaaca atttcgggcc cctgcgtgtt cttctgaggt tcatctttta catttgcttc      60
tgctggataa ttttcagagg caacaaggaa aaattagatg gcaaaaagtc gtctttcaag    120
gaaaaatccc caccatcttt cgagatcccc tgtaacttat tggcaactga agaatgaaa     180 aggaggaaaa tacaaaatat actagaactg aaaaaaaaaa agtataaata gagacgatat    240
atgccaatac ttcacaatgt tcgaatctat tcttcatttg cagctattgt aaaataataa    300
aacatcaaga acaaacaagc tcaacttgtc ttttctaaga acaagaata acacaaaaa     360 caaaagtttt ttttaatttt aatcaaaaaa tgccgtcggg cttccaacag ataggctccg    420
aagatgggga acccctcag cagcgagtga ctgggaccct ggtccttgct gtgttctctg     480
cggtgcttgg ctccctgcag tttgggtaca acattggggt catcaatgcc cctcagaagg    540
tgattgaaca gagctacaat gagacgtggc tgggaggca ggggcctgag ggacccagct     600
ccatccctcc aggcaccctc accaccctct gggccctctc catggccatc ttttccgtgg    660
gcggcatgat ttcctccttc ctcattggta tcatctctca gtggcttgga aggaaaaggg    720
ccatgctggt caacaatgtc ctggcggtgc tgggggggcag cctcatgggc ctggccaacg    780
ctgctgcctc ctatgaaatg ctcatccttg acgattcct cattggcgcc tactcagggc    840
tgacatcagg gctggtgccc atgtacgtgg gggagattgc tcccactcac ctgcggggcg    900
ccctggggac gctcaaccaa ctggccattg ttatcgcat tctgatcgcc caggtgctgg    960
gcttggagtc cctcctgggc actgccagcc tgtggccact gctcctgggc tcacagtgc    1020 tacctgccct cctgcagctg gtcctgctgc ccttctgtcc cgagagcccc cgctacctct    1080
acatcatcca gaatctcgag gggcctgcca gaaagagtct gaagcgcctg acaggctggg    1140
ccgatgtttc tggagtgctg gctgagctga aggatgagaa gcggaagctg agcgtgagc    1200 ggccactgtc cctgctccag ctcctgggca gccgtaccca ccggcagccc ctgatcattg    1260
cggtcgtgct gcagctgagc cagcagctct tggcatcaa tgctgttttc tattattcga    1320
ccagcatctt cgagacagca ggggtaggcc agcctgccta tgccaccata ggagctggtg    1380
```

```
tggtcaacac agtcttcacc ttggtctcgg tgttgttggt ggagcgggcg gggcgccgga    1440
cgctccatct cctgggcctg gcgggcatgt gtggctgtgc catcctgatg actgtggctc    1500
tgctcctgct ggagcgagtt ccagccatga gctacgtctc cattgtggcc atctttggct    1560
tcgtggcatt ttttgagatt ggccctggcc ccattccttg gttcatcgtg gccgagctct    1620
tcagccaggg accccgcccg gcagccatgg ctgtggctgg tttctccaac tggacgagca    1680
acttcatcat tggcatgggt ttccagtatg ttgcggaggc tatggggccc tacgtcttcc    1740
ttctatttgc ggtcctcctg ctgggcttct tcatcttcac cttcttaaga gtacctgaaa    1800
ctcgaggccg gacgtttgac cagatctcag ctgccttcca ccggacaccc tctcttttag    1860
agcaggaggt gaaacccagc acagaacttg agtatttagg gccagatgag aacgactgac    1920
tcgagtcatg taattagtta tgtcacgctt acattcacgc cctcccccca catccgctct    1980
aaccgaaaag gaaggagtta gacaacctga agtctaggtc cctatttatt tttttatagt    2040
tatgttagta ttaagaacgt tatttatatt tcaaattttt ctttttttttc tgtacagacg    2100 cgtgtacgca tgtaacatta tactgaaaac cttgcttgag aaggttttgg gacgctcgaa    2160
ggctttaatt tgcggccggt acccaattcg ccctatagtg agtcgtatta cgcgcgctca    2220
ctggccgtcg ttttacaacg tcgtgactgg gaaaaccctg gcgttaccca acttaatcgc    2280
cttgcagcac atcccccttt cgccagctgg cgtaatagcg aagaggcccg caccgatcgc    2340
ccttcccaac agttgcgcag cctgaatggc gaatggcgcg acgcgccctg tagcggcgca    2400
ttaagcgcgg cgggtgtggt ggttacgcgc agcgtgaccg ctacacttgc cagcgcccta    2460
gcgcccgctc ctttcgcttt cttcccttcc tttctcgcca cgttcgccgg ctttccccgt    2520
caagctctaa atcgggggct ccctttaggg ttccgattta gtgctttacg cacctcgac    2580 cccaaaaaac ttgattaggg tgatggttca cgtagtgggc catcgccctg atagacggtt    2640
tttcgccctt tgacgttgga gtccacgttc tttaatagtg gactcttgtt ccaaactgga    2700
acaacactca accctatctc ggtctattct tttgatttat aagggatttt gccgatttcg    2760
gcctattggt taaaaaatga gctgatttaa caaaaattta acgcgaattt taacaaaata    2820
ttaacgttta caatttcctg atgcggtatt ttctccttac gcatctgtgc ggtatttcac    2880
accgcatagg gtaataactg atataattaa attgaagctc taatttgtga gtttagtata    2940
catgcattta cttataatac agttttttag ttttgctggc cgcatcttct caaatatgct    3000
tcccagcctg ctttttctgta acgttcaccc tctaccttag catcccttcc ctttgcaaat    3060
agtcctcttc caacaataat aatgtcagat cctgtagaga ccacatcatc cacggttcta    3120
tactgttgac ccaatgcgtc tcccttgtca tctaaaccca caccgggtgt cataatcaac    3180
caatcgtaac cttcatctct tccacccatg tctctttgag caataaagcc gataacaaaa    3240
tctttgtcgc tcttcgcaat gtcaacagta cccttagtat attctccagt agatagggag    3300
cccttgcatg acaattctgc taacatcaaa aggcctctag gttcctttgt tacttcttct    3360
gccgcctgct tcaaaccgct aacaatacct gggcccacca caccgtgtgc attcgtaatg    3420
tctgcccatt ctgctattct gtatacaccc gcagagtact gcaatttgac tgtattacca    3480
atgtcagcaa attttctgtc ttcgaagagt aaaaaattgt acttggcgga taatgccttt    3540
agcggcttaa ctgtgccctc catggaaaaa tcagtcaaga tatccacatg tgtttttagt    3600
aaacaaattt tgggacctaa tgcttcaact aactccagta attccttggt ggtacgaaca    3660
tccaatgaag cacacaagtt tgtttgcttt tcgtgcatga tattaaatag cttggcagca    3720
acaggactag gatgagtagc agcacgttcc ttatatgtag ctttcgacat gatttatctt    3780
```

```
cgtttcctgc aggttttgt tctgtgcagt tgggttaaga atactgggca atttcatgtt      3840
tcttcaacac tacatatgcg tatatatacc aatctaagtc tgtgctcctt ccttcgttct      3900
tccttctgtt cggagattac cgaatcaaaa aaatttcaaa gaaaccgaaa tcaaaaaaaa      3960
gaataaaaaa aaaatgatga attgaattga aaagctgtgg tatggtgcac tctcagtaca      4020
atctgctctg atgccgcata gttaagccag ccccgacacc cgccaacacc cgctgacgcg      4080
ccctgacggg cttgtctgct cccggcatcc gcttacagac aagctgtgac cgtctccggg      4140
agctgcatgt gtcagaggtt ttcaccgtca tcaccgaaac gcgcgagacg aaagggcctc      4200
gtgatacgcc tatttttata ggttaatgtc atgataataa tggtttctta gtatgatcca      4260
atatcaaagg aaatgatagc attgaaggat gagactaatc caattgagga gtggcagcat      4320
atagaacagc taaagggtag tgctgaagga agcatacgat accccgcatg gaatgggata      4380
atatcacagg aggtactaga ctacctttca tcctacataa atagacgcat ataagtacgc      4440
atttaagcat aaaacacgcac tatgccgttc ttctcatgta tatatatata caggcaacac      4500
gcagatatag gtgcgacgtg aacagtgagc tgtatgtgcg cagctcgcgt tgcattttcg      4560
gaagcgctcg ttttcggaaa cgctttgaag ttcctattcc gaagttccta ttctctagaa      4620
agtataggaa cttcagagcg cttttgaaaa ccaaaagcgc tctgaagacg cactttcaaa      4680
aaaccaaaaa cgcaccggac tgtaacgagc tactaaaata ttgcgaatac cgcttccaca      4740
aacattgctc aaaagtatct ctttgctata tatctctgtg ctatatccct atataaccta      4800
cccatccacc tttcgctcct tgaacttgca tctaaactcg acctctacat tttttatgtt      4860
tatctctagt attactcttt agacaaaaaa attgtagtaa gaactattca tagagtgaat      4920
cgaaaacaat acgaaaatgt aaacatttcc tatacgtagt atatagagac aaaatagaag      4980
aaaccgttca taattttctg accaatgaag aatcatcaac gctatcactt tctgttcaca      5040
aagtatgcgc aatccacatc ggtatagaat ataatcgggg atgcctttat cttgaaaaaa      5100
tgcacccgca gcttcgctag taatcagtaa acgcgggaag tggagtcagg ctttttttat      5160
ggaagagaaa atagacacca aagtagcctt cttctaacct taacggacct acagtgcaaa      5220
aagttatcaa gagactgcat tatagagcgc acaaggagaa aaaaagtaa tctaagatgc      5280 tttgttagaa aaatagcgct ctcgggatgc attttttgtag aacaaaaaag aagtatagat      5340
tctttgttgg taaaatagcg ctctcgcgtt gcatttctgt tctgtaaaaa tgcagctcag      5400
attctttgtt tgaaaaatta gcgctctcgc gttgcatttt tgttttacaa aaatgaagca      5460
cagattcttc gttggtaaaa tagcgctttc gcgttgcatt tctgttctgt aaaaatgcag      5520
ctcagattct ttgtttgaaa aattagcgct ctcgcgttgc attttttgttc tacaaaatga      5580 agcacagatg cttcgttcag gtggcacttt tcggggaaat gtgcgcggaa ccccctatttg      5640 tttatttttc taaatacatt caaatatgta tccgctcatg agacaataac cctgataaat      5700
gcttcaataa tattgaaaaa ggaagagtat gagtattcaa catttccgtg tcgcccttat      5760
tccctttttt gcggcatttt gccttcctgt ttttgctcac ccagaaacgc tggtgaaagt      5820
aaaagatgct gaagatcagt tgggtgcacg agtgggttac atcgaactgg atctcaacag      5880
cggtaagatc cttgagagtt ttcgccccga agaacgtttt ccaatgatga gcacttttaa      5940
agttctgcta tgtggcgcgg tattatcccg tattgacgcc gggcaagagc aactcggtcg      6000
ccgcatacac tattctcaga atgacttggt tgagtactca ccagtcacag aaaagcatct      6060 tacgatggc atgacagtaa gagaattatg cagtgctgcc ataaccatga gtgataacac      6120
tgcggccaac ttacttctga caacgatcgg aggaccgaag gagctaaccg cttttttgca      6180
```

```
caacatgggg gatcatgtaa ctcgccttga tcgttgggaa ccggagctga atgaagccat    6240
accaaacgac gagcgtgaca ccacgatgcc tgtagcaatg caacaacgt tgcgcaaact    6300 attaactggc gaactactta ctctagcttc ccggcaacaa ttaatagact ggatggaggc    6360
ggataaagtt gcaggaccac ttctgcgctc ggcccttccg gctggctggt ttattgctga    6420
taaatctgga gccggtgagc gtgggtctcg cggtatcatt gcagcactgg ggccagatgg    6480
taagccctcc cgtatcgtag ttatctacac gacggggagt caggcaacta tggatgaacg    6540
aaatagacag atcgctgaga taggtgcctc actgattaag cattggtaac tgtcagacca    6600
agtttactca tatatacttt agattgattt aaaacttcat tttaatta aaaggatcta    6660 ggtgaagatc cttttgata atctcatgac caaaatccct taacgtgagt tttcgttcca    6720
ctgagcgtca gacccgtag aaaagatcaa aggatcttct tgagatcctt ttttctgcg    6780 cgtaatctgc tgcttgcaaa caaaaaaacc accgctacca gcggtggttt gtttgccgga    6840
tcaagagcta ccaactcttt ttccgaaggt aactggcttc agcagagcgc agataccaaa    6900
tactgtcctt ctagtgtagc cgtagttagg ccaccacttc aagaactctg tagcaccgcc    6960
tacatacctc gctctgctaa tcctgttacc agtggctgct gccagtggcg ataagtcgtg    7020
tcttaccggg ttggactcaa gacgatagtt accggataag gcgcagcggt cgggctgaac    7080
ggggggttcg tgcacacagc ccagcttgga gcgaacgacc tacaccgaac tgagatacct    7140
acagcgtgag ctatgagaaa gcgccacgct tcccgaaggg agaaaggcgg acaggtatcc    7200
ggtaagcggc agggtcggaa caggagagcg cacgagggag cttccagggg gaaacgcctg    7260
gtatctttat agtcctgtcg ggtttcgcca cctctgactt gagcgtcgat ttttgtgatg    7320
ctcgtcaggg gggcggagcc tatggaaaaa cgccagcaac gcggccttt tacggttcct    7380 ggccttttgc tggccttttg ctcacatgtt ctttcctgcg ttatcccctg attctgtgga    7440
taaccgtatt accgcctttg agtgagctga taccgctcgc cgcagccgaa cgaccgagcg    7500
cagcgagtca gtgagcgagg aagcggaaga gcgcccaata cgcaaaccgc ctctccccgc    7560
gcgttggccg attcattaat gcagctggca cgacaggttt cccgactgga aagcgggcag    7620
tgagcgcaac gcaattaatg tgagttacct cactcattag gcaccccagg ctttacactt    7680
tatgcttccg gctcctatgt tgtgtggaat tgtgagcgga taacaatttc acacaggaaa    7740
cagctatgac catgattacg ccaagcgcgc aattaaccct cactaagggg aacaaaagct    7800
ggagcttttt                                                          7809
```

USE OF *SACCHAROMYCES CEREVISIAE* ERG4 MUTANTS FOR EXPRESSING MAMMALIAN GLUCOSE TRANSPORTERS

This application is a continuation of U.S. patent application Ser. No. 11/775,384, filed on Jul. 10, 2007, which issued as U.S. Pat. No. 7,615,360 on Nov. 10, 2009; which is a continuation of U.S. patent application Ser. No. 10/659,234, filed on Sep. 10, 2003, which issued as U.S. Pat. No. 7,244,821 on Jul. 17, 2007; which claims priority from U.S. Provisional Patent Application No. 60/455,340, filed on Mar. 17, 2003, now expired, and German Patent Application No. 10242763.1, filed on Sep. 14, 2002, each of which is incorporated, herein, in their entireties.

The invention relates to yeast strains in which the human Glut 4 and Glut 1 transporters can be functionally expressed.

Most heterotropic cells transport glucose via special transporter proteins into the cell interior. The various organisms have developed different mechanisms mediating the transporting of glucose, such as, in particular, proton symport systems, $Na^+$ glucose transporters, binding protein-dependent systems, phosphotransferase systems, and systems for facilitated diffusion. In the eukaryotes, a family of glucose transporters which are encoded in mammals by the GLUT genes (GLUT=glucose transporter) and *Saccharomyces cerevisiae* by the HXT genes (HXT=hexose transporter) mediates glucose uptake via facilitated diffusion. Said transporters belong to a larger family of sugar transporters. They are characterized by the presence of 12 transmembrane helices and by a plurality of conserved amino acid radicals. Glucose transport plays an important part in disorders associated with a defective glucose homeostasis, such as, for example, diabetes mellitus or Fanconi-Bickel syndrome. The glucose transport in mammals has therefore been the subject of numerous studies. To date, thirteen glucose transporter-like proteins have been identified (GLUT1 to GLUT12, HMIT—H-myo-inositol transporter)). Said transporters play key parts which include the uptake of glucose into various tissues, its storage in the liver, its insulin-dependent uptake into muscle cells and adipocytes and glucose measurement by the β cells of the pancreas.

GLUT1 mediates the transport of glucose into erythrocytes and through the blood-brain barrier, but is also expressed in many other tissues, while GLUT4 is limited to insulin-dependent tissues, primarily to muscle and fatty tissue. In said insulin-dependent tissues, controlling the targeting of GLUT4 transporters through intracellular compartments or plasma membrane compartments represents an important mechanism for regulating glucose uptake. In the presence of insulin, intracellular GLUT 4 is redistributed through the plasma membrane in order to facilitate glucose uptake. GLUT1 is likewise expressed in said insulin-dependent tissues, and its distribution in the cell is likewise influenced by insulin, albeit not as strongly. In addition, the relative efficacy with which GLUT1 or GLUT4 catalyze sugar transport is determined not only by the extent of the targeting of each transporter to the cell surface but also by their kinetic properties.

The fact that different glucose transporter isoforms are coexpressed and the rapid glucose metabolism have rendered studies on the role and the exact properties of each glucose transporter isoform in these insulin-dependent tissues complicated. In order to solve these problems, heterologous expression systems such as *Xenopus* oocytes, tissue culture cells, insect cells and yeast cells have been used. However, it turned out that a number of difficulties appeared in connection with these systems: too weak an activity of the heterologously expressed transporters, intrinsic glucose transporters in said systems, intracellular retention of a considerable proportion of the transporters or even production of inactive transporters.

Naturally occurring GLUT4 protein of mammals, in particular that of humans, can be expressed in a functional manner in strains of *Saccharomyces cerevisiae* under particular conditions.

Yeast cells are unicell eukaryotic organisms. They are therefore, for some proteins, more suitable for expression than bacterial systems, in particular with regard to carrying out screen assays for identifying pharmaceutically active substances.

The present invention relates to a purified and isolated polynucleotide comprising a DNA sequence which codes for the GLUT4V85M protein.

Said protein contains at position 85 of the amino acid chain of the human GLUT4 protein an amino acid exchange from valine to methionine. This altered GLUT4V85M protein provides further alternatives for expressing a functional GLUT4 protein. A GLUT4 protein should be regarded as functional in connection with *Saccharomyces cerevisiae* if glucose uptake can be observed in a *Saccharomyces cerevisiae* strain whose glucose transporters in their entirety are inactive (=hxt(-)) after expression of said GLUT4 protein. Glucose uptake may be determined either by transport measurements by means of radioactively labeled glucose or by growth on medium with glucose as sole carbon source.

In a preferred embodiment, the purified and isolated polynucleotide comprising a DNA sequence which calls for a protein GLUT4V85M may include or comprise a sequence of the following groups:

a) a nucleotide sequence according to Seq ID No. 1,
b) a nucleotide sequence which hybridizes to a sequence of Seq ID No. 1 under stringent conditions and which codes for a protein GLUT4V85M.

The purified and isolated polynucleotide preferably encodes a GLUT4V85M protein which has an amino acid sequence of Seq ID No. 2.

The purified and isolated polynucleotide comprising a DNA sequence which codes as discussed previously for a protein GLUT4V85M, may be operationally linked to a promotor. Suitable promotors are in particular prokaryotic or eukaryotic promoters such as, for example, the Lac-, trp-, ADH- or HXT7 promotor. The part of the polynucleotides, which codes for the protein GLUT4V85M is operationally linked to a promotor precisely if a bacterial or eukaryotic organism produces, by means of said promotor with the aid of a vector, an mRNA which can be translated into the protein GLUT4V85M. An example of such a vector is the vector p4H7GLUT4V85M (Seq ID No. 3). The protein GLUT4V85M may be expressed in yeast cells by means of said vector.

The above-described polynucleotide comprising a DNA sequence which codes for a protein GLUT4V85M is, in a preferred embodiment, suitable for replicating said polynucleotide in a yeast cell or for expressing the part of the polynucleotide, which encodes the protein GLUT4V85M, in a yeast cell to give the protein GLUT4V85M. A yeast cell from *Saccharomyces cerevisiae* is particularly suitable. For replication and expression in a yeast cell, the polynucleotide comprising a DNA sequence which calls for a protein GLUT4V85M is present in the form of a yeast vector. The polynucleotide region coding for the GLUT4V85M protein may be operationally linked to a yeast cell-specific promotor such as, for example, the ADH promotor (alcohol dehydrogenase promotor) or the HXT7 promotor (hexose-transporter promotor). The yeast sectors are a group of vectors which was developed for cloning of DNA in yeasts.

The invention furthermore relates to a yeast cell from *Saccharomyces cerevisiae* in which all glucose transporters are no longer functional (=hxt (−)) and which contains no functional Erg4 protein. Such a yeast cell is preferably a yeast cell deposited as *Saccharomyces cerevisiae* DSM 15187 with the DSMZ (Deutsche Sammlung von Mikroorganismen and Zellkulturen GmbH, Mascheroder Weg 16, 38124 Brunswick, Germany).

The invention also relates to a yeast cell in which all glucose transporters are no longer functional and which contains no functional Fgy1 and no functional Erg4 protein. The lack of an Erg4 protein or of an Fgy1 protein may be attributed in particular to an interruption of the corresponding coding genome sections or to a partial or complete removal of said coding genome sections.

Preference is given to using as yeast cell which contains no functional glucose transporters, no functional Fgy1 protein and no functional Erg4 protein, a yeast cell as deposited with the DSMZ as *Saccharomyces cerevisiae* DSM 15184.

A yeast cell as described above is preferably used for expressing a mammalian GLUT1 protein or a mammalian GLUT4 protein, in particular a protein from rats, mice, rabbits, pigs, cattle or primates. A preferred embodiment uses the yeast cell for expressing a human GLUT4 or GLUT1 protein.

A *Saccharomyces cerevisiae* yeast cell whose glucose transporters in their entirety and also the Erg4 protein are no longer functional may contain a polynucleotide of the present invention, which comprises a DNA sequence coding for a protein GLUT4V85M. Said yeast cell can also express the GLUT4V85M protein and thus contain said protein.

A yeast strain of this kind, containing a polynucleotide which comprises a DNA sequence coding for the GLUT4V85M protein, is preferably the *Saccharomyces cerevisiae* DSM 15185 yeast strain which has been deposited with the DMSZ.

A yeast cell whose glucose transporters in their entirety and also the Erg4 protein are no longer functional and which contains a polynucleotide comprising a DNA sequence which calls for a protein GLUT4V85M may be prepared, for example, by
  a) providing a yeast cell whose glucose transporters in their entirety and also the Erg4 protein are no longer functional,
  b) providing an isolated and purified polynucleotide which comprises a DNA sequence coding for the GLUT4V85M protein and which can be replicated in the yeast cell,
  c) transforming the yeast cell from a) with the polynucleotide from b),
  d) selecting a transformed yeast cell,
  e) where appropriate expressing the GLUT4V85M protein.

An isolated and purified polynucleotide which comprises a DNA sequence coding for the GLUT4V85M protein is preferably a vector which can be replicated in a yeast cell and in which said DNA sequence was cloned. An example of such a vector is p4H7GLUT4V85M (Seq ID No. 3).

The invention also relates to a yeast cell whose glucose transporters in their entirety and whose proteins for Fgy1 and Erg4 are no longer functional and which contains a polynucleotide which comprises a DNA sequence coding for the GLUT4V85M protein. Said yeast cell can also express the GLUT4V85M protein and thus contain said protein. A yeast strain of this kind is preferably the *Saccharomyces cerevisiae* DSM 15186 deposited with the DSMZ.

A yeast cell whose glucose transporters in their entirety and also the proteins Fgy1 and Erg4 are no longer functional and which contains a polynucleotide comprising a DNA sequence which codes for the GLUT4V85M protein may be prepared, for example, by
  a) providing a yeast cell whose glucose transporters in their entirety and also the proteins Fgy1 and Erg4 are no longer functional,
  b) providing an isolated and purified polynucleotide which comprises a DNA sequence coding for the GLUT4V85M protein and which can be replicated in the yeast cell,
  c) transforming the yeast cell from a) with the polynucleotide from b),
  d) selecting a transformed yeast cell,
  e) where appropriate expressing the GLUT4V85M protein.

The abovementioned isolated and purified polynucleotide which comprises a DNA sequence coding for the GLUT4V85M protein is preferably a vector which can be replicated in a yeast cell and in which said DNA sequence was cloned. An example of such a vector is p4H7GLUT4V85M (Seq ID No. 3).

The invention also relates to a yeast cell whose glucose transporters in their entirety are no longer functional and which contains a polynucleotide comprising a DNA sequence which calls for the GLUT4V85M protein.

Said yeast cell can also express the GLUT4V85M protein and thus contain said protein. A preferred yeast strain of this kind is the *Saccharomyces cerevisiae* 15188 yeast strain deposited with the DSMZ.

A yeast cell whose glucose transporters in their entirety are no longer functional and which contains a polynucleotide comprising a DNA sequence which codes for the GLUT4V85M protein may be prepared, for example, by
  a) providing a yeast cell whose glucose transporters in their entirety are no longer functional,
  b) providing an isolated and purified polynucleotide which comprises a DNA sequence coding for the GLUT4V85M protein and which can be replicated in the yeast cell,
  c) transforming the yeast cell from a) with the polynucleotide from b),
  d) selecting a transformed yeast cell,
  e) where appropriate expressing the GLUT4V85M protein.

An isolated and purified polynucleotide which comprises a DNA sequence coding for the GLUT4V85M protein is preferably a vector which can be replicated in a yeast cell and in which said DNA sequence was cloned. An example of such a vector is p4H7GLUT4V85M (Seq ID No. 3).

The invention also relates to a protein having the amino acid sequence according to Seq ID No. 2. Said protein is a human GLUT4 protein in which a valine has been replaced by a methionine in position 85 of the amino acid chain.

The invention also relates to a method for identifying a compound which stimulates the activity of a GLUT4 protein, which method comprises the steps
  a) providing a yeast cell whose glucose transporters in their entirety and also Erg4 protein are no longer functional and which contains a polynucleotide comprising a DNA sequence which codes for a protein GLUT4V85M,
  b) providing a chemical compound,
  c) contacting the yeast of a) with the chemical compound of b),
  d) determining glucose uptake by the yeast of c), e) relating the detected value of the glucose uptake of d) to the detected value of glucose uptake in a yeast cell as claimed in a) which has been contacted with a chemical compound as claimed in b), with a compound which causes an increase in the amount of glucose taken up in the yeast as claimed in d) stimulating the activity of said GLUT4 protein. Compounds which stimulate the activity of the GLUT4V85M protein can be assumed to stimulate also the GLUT4 activity.

The invention also relates to a pharmaceutical which contains a compound which has been identified by the method described above and furthermore to additives and excipients for formulating a pharmaceutical. Furthermore, the invention relates to the use of a compound which has been identified by the method described above for producing a pharmaceutical for the treatment of type I and/or II diabetes.

The invention also relates to a pharmaceutical comprising a compound which has been identified by the method described above and to additives and excipients for formulating a pharmaceutical. Furthermore, the invention relates to the use of a compound identified by the method described above for producing a pharmaceutical for the treatment of diabetes.

The invention furthermore relates to the use of a compound identified by a method described above for producing a pharmaceutical for the treatment of diabetes.

The present invention also comprises a method for identifying a compound which inhibits the protein encoded by the Erg4 gene, which method comprises the steps:
a) providing a yeast cell whose glucose transporters in their entirety and no longer functional and which contains a polynucleotide comprising a DNA sequence which codes for the GLUT4V85M protein and can be replicated in a yeast cell,
b) providing a chemical compound
c) contacting the yeast of a) with the chemical compound of b),
d) determining glucose uptake by the yeast of c),
e) relating the detected value of the glucose uptake of d) to the detected value of glucose uptake in a yeast cell as claimed in a) which is not contacted with a chemical compound as claimed in b), with a compound which causes an increase in the amount of glucose taken up in the yeast as claimed in d) stimulating the activity of a protein Erg4.

The invention furthermore relates to a method for identifying a compound inhibiting the corresponding protein of the Fgy1 gene, which comprises the steps:
a) providing a yeast cell whose glucose transporters in their entirety and whose Erg4 protein are no longer functional and which contains a GLUT4 protein,
b) providing a chemical compound
c) contacting the yeast of a) with the chemical compound of b),
d) determining glucose uptake by the yeast of c),
e) relating the detected value of the glucose uptake of d) to the detected value of glucose uptake in a yeast cell as claimed in a) which is not contacted with a chemical compound as claimed in b), with a compound which causes an increase in the amount of glucose taken up in the yeast as claimed in d) stimulating the activity of a protein Fgy1.

The invention also relates to a pharmaceutical comprising a compound which has been identified by the method described above and to additives and excipients for formulating a pharmaceutical.

The invention may be illustrated in more detail below with respect to technical details.

Hybridization means the assembling of two nucleic acid single strands having complementary base sequences to double strands. Hybridization may take place between two DNA strands, one DNA and one RNA strand and between two RNA strands. In principle, it is possible to prepare hybrid molecules by heating the nucleic acids involved which may initially be in double-stranded form, by boiling, for example, in a waterbath for 10 minutes, until they disintegrate into single-stranded molecules without secondary structure. Subsequently, they can be cooled slowly. During the cooling phase, complementary chains pair to give double-stranded hybrid molecules. Under laboratory conditions, hybridizations are usually carried out with the aid of hybridization filters to which single-stranded or denaturable polynucleotide molecules are applied by blotting or electrophoresis. It is possible to visualize the hybridization using appropriate complementary polynucleotide molecules by providing said polynucleotide molecules to be hybridized with a radioactive fluorescent label. Stringency describes the degree of matching or alignment of particular conditions. High stringency has higher demands on matching than low stringency. Depending on the application and objective, particular conditions with different stringency are set for the hybridization of nucleic acids. At high stringency, the reaction conditions for the hybridization are set in such a way that only complementary molecules which match very well can hybridize with one another. Low stringency enables molecules also to partially hybridize with relatively large sections of unpaired or mispaired bases.

The hybridization conditions are to be understood as being stringent, in particular, if the hybridization is carried out in an aqueous solution containing 2×SSC at 68° C. for at least 2 hours, followed by washing first in 2×SSC/0.1% SDS at room temperature for 5 minutes, then in 1×SSC/0.1% SDS at 68° C. for 1 hour and then in 0.2% SSC/0.1% SDS at 68° C. for another hour.

A 2×SSC, 1×SSC or 0.2×SSC solution is prepared by diluting a 20×SSC solution appropriately. A 20×SSC solution contains 3 mol/l NaCl and 0.3 mol/l Na citrate. The pH is 7.0. The skilled worker is familiar with the methods for hybridizations of polynucleotides under stringent conditions. Appropriate instructions can be found in specialist books such as, in particular, Current Protocols in Molecular Biology (Wiley Interscience; editors: Frederich M. Ausubel, Roger Brant, Robert E. Kingston, David J. Moore, J. G. Seidmann, Kevin Struhl; ISBN: 0-471-50338-X).

The yeast vectors can be divided into different subgroups. YIp vectors (yeast integrating plasmids) essentially correspond to the vectors used in bacteria for clonings, but contain a selectable yeast gene (e.g. URA3, LEU2).

Only when the foreign DNA integrates into a yeast chromosome after introduction of said vector, are these sequences replicated together with the chromosome and, with the formation of a clone, stably transferred to all daughter cells.

Based on this method, plasmids have been derived which can replicate autonomously owing to eukaryotic ORIs (origins of replication). Such yeast vectors are referred to as YRp vectors (yeast replicating plasmids) or ARS vectors (autonomously replicating sequence).

Furthermore, there are YEp vectors (yeast episomal plasmids) which are derived from the yeast 2 μm plasmid and which contain a selective marker gene. The class of the YAC vectors (yeast artificial chromosome) behave like independent chromosomes.

A yeast vector containing a gene to be expressed is introduced into the yeast by means of transformation in order for said gene to be able to be expressed. Examples of methods suitable for this purpose are electroporation or incubation of competent cells with vector DNA. Suitable yeast expression promoters are known to the skilled worker, examples being the SOD1 promotor (superoxide dismutase), ADH promotor (alcohol dehydrogenase), the promotor of the gene for acidic phosphatase, HXT2 promotor (glucose transporter 2), HXT7 promotor (glucose transporter 7), GAL2 promotor (galactose transporter) and others. The construct comprising a yeast expression promotor and a gene to be expressed (e.g. GLUT4V85M) is, for the purpose of expression, part of a yeast vector. To carry out expression, said yeast vector may be a self-replicating particle which is independent of the yeast genome or may be stably integrated into the yeast genome. A suitable yeast vector is in principle any polynucleotide sequence which can be propagated in a yeast. Yeast vectors which may be used are in particular yeast plasmids or yeast artificial chromosomes. Yeast vectors usually contain an origin of replication (2μ, ars) or starting the replication process and a selection marker which usually comprises an auxotrophy marker or an antibiotic resistance gene. Examples of yeast vectors known to the skilled worker are pBM272, pCS19, pEMBCYe23, pFL26, pG6, pNN414, pTV3, p426MET25, p4H7 and others.

In accordance with the present invention, selection of a cell means the specific concentration thereof, owing to a selection marker such as, for example, resistance to an antibiotic or the ability to grow on a particular minimal medium, and furthermore the isolation and subsequent cultivation thereof on an agar plate or in submerged culture.

Cultivation, transformation and selection of a transformed yeast cell and also expression of a protein in a yeast cell are among the methods commonly used by the skilled worker. Instructions regarding said methods can be found in standard text books, for example in Walker Graeme M.: Yeast Physiology and Biotechnology, Wiley and Sons, ISBN: 0-471-9446-8 or in Protein Synthesis and Targeting in Yeast, Ed. Alistair J. P. Brown, Mick F. Fruite and John E. G. Mc Cartly; Springer Berlin; ISBN: 3-540-56521-3 or in "Methods in Yeast Genetics, 1997: A Cold Spring Harbor Laboratory Course Manual; Adams Alison (Edt.); Cold Spring Harbor Laboratory; ISBN: 0-87969-508-0".

The yeast *Saccharomyces cerevisiae* has 17 known hexose transporters and additionally three known maltose transporters, which are capable of transporting hexoses into said yeast, provided that their expression is sufficiently high. In one known strain all transporters suitable for hexose uptake were removed by deletion. Said strain contains merely just the two genes MPH2 and MPH3 which are homologous to maltose transport proteins. The two genes MPH2 and MPH3 are repressed in the presence of glucose in the medium. Wieczorke et al., FEBS Lett. 464, 123-128 (1999) describe the preparation and characterization of this yeast strain. Said strain is not able to propagate on a substrate containing glucose as sole carbon source. It is possible to select from said strain mutants which functionally express GLUT1, starting from a corresponding vector (hxt fgy1-1 strain).

If the yeast strain hxt fgy1-1 is transformed with a plasmid vector which carries a GLUT4 gene under control of a yeast promotor, still only very little glucose is transported. Functional GLUT4 expression requires further adjustments to this yeast strain in order to make possible a significant glucose transport by means of GLUT4. Such yeast strains whose cells take up glucose by means of a single glucose transporter GLUT4 can be isolated on substrates having glucose as sole carbon source. For this purpose, a yeast hxt fgy1-1 strain carrying a GLUT4 gene under the functional control of a yeast promotor is transformed. These yeast cells transformed in this way are applied to a nutrient medium containing glucose as sole carbon source and are incubated thereon. After a few days of incubation at, for example 30° C., the growth of individual colonies is observed. One of these colonies is isolated. The removal of the yeast plasmid from said colony prevents propagation on the nutrient medium containing glucose as sole carbon source. If this strain which no longer contains a vector plasmid is again transformed with a yeast vector carrying a GLUT4 gene under the functional control of a yeast promotor, said strain is then again able to propagate on a medium containing glucose as sole carbon source.

The abovementioned yeast strains are the subject matter of International Application PCT/EP02/01373, filed on Feb. 9, 2002, which claims the priority of DE 10106718.6 of Feb. 14, 2002.

Yeast strains whose indigenous transporters for hexoses (glucose transporters) in their entirety are no longer functional have already been deposited at an earlier date in connection with International Application PCT/EP02/01373 with the Deutsche Sammlung von Mikroorganismen and Zellkulturen GmbH (DSMZ) under the number DSM 14035, DSM 14036 or DSM 14037.

The polynucleotide and amino acid sequences of GLUT4 are accessible, for example, via the following entries in gene banks M20747 (cDNA; human), EMBL: D28561 (cDNA; rat), EMBL: M23382 (cDNA; mouse), Swissprot: P14672 (protein; human), Swissprot: P19357 (protein; rat) and Swissprot: P14142 (protein; mouse).

Polynucleotide sequences and amino acid sequences of GLUT1 are disclosed under the following code numbers of the databases indicated: EMBL: M20653 (cDNA; human), EMBL: M13979 (cDNA; rat), EMBL: M23384 (cDNA; mouse), Swissprot: P11166 (protein; human), Swissprot: P11167 (protein; rat) and Swissprot: P17809 (protein; mouse).

Pharmaceuticals are dosage forms of pharmacologically active substances for the therapy of diseases or bodily malfunctions in humans and animals. Examples of dosage forms for oral therapy are powders, granules, tablets, pills, lozenges, sugar-coated tablets, capsules, liquid extracts, tinctures and syrups. Examples which are used for external application are aerosols, sprays, gels, ointments or powders. Injectable or infusible solutions allow parenteral administration, using vials, bottles or prefilled syringes. These and other pharmaceuticals are known to the skilled worker in the field of pharmaceutical technology.

Excipients for formulating a pharmaceutical made possible the preparation of the active substance with the purpose of optimizing the application, distribution and development of action of the active ingredient for the particular application. Examples of such excipients are fillers, binders, disintegrants or glidants, such as lactose, sucrose, mannitol, sorbitol, cellulose, starch, dicalcium phosphate, polyglycols, alginates, polyvinylpyrrolidone, carboxymethylcellulose, talc or silicon dioxide.

Diabetes manifests itself by the excretion of glucose together with the urine with an abnormal increase in the blood glucose level (hyperglycaemia), owing to a chronic metabolic condition due to insulin deficiency or reduced insulin action. The lack of, or reduced, insulin action leads to insufficient absorption and conversion by the cells of the glucose taken up into the blood. In fatty tissue, insulin-antagonistic hormones have the effect of increasing lypolysis accompanied by an increase in the free fatty acid levels in the blood.

Adiposity (obesity) is the abnormal weight gain owing to an energy imbalance due to excessive intake of calories, which constitutes a health risk.

The amount of a hexose which is taken up by a provided yeast strain as described just above can be determined by means of uptake studies using radioactively labeled glucose. For this purpose, a particular amount of the yeast cells is suspended in, for example, 100 µl of a buffer, for example at a concentration of 60 mg (wet weight) per ml, and admixed with a defined amount of $^{14}$C- or $^{3}$H-labeled glucose as sole carbon source. The cells are incubated, and defined amounts thereof are removed at specific times. The amount of glucose taken up is determined with the aid of LSC (Liquid Scintillation Counting). The amount of a hexose which is taken up by a yeast strain provided and as just described above may, however, also be determined by means of a growth assay on media containing glucose as sole carbon source. For this purpose, the rate of growth of the strain is determined, after addition of the compound, for example by measuring the optical density of the culture at 600 nm at regular intervals, and this value is compared with the rate of growth of a control strain (e.g. yeast wild-type strain).

A compound is provided, in particular, by chemical synthesis or by isolating chemical substances from biological organisms. It is also possible to carry out chemical synthesis in an automated manner. The compounds obtained by synthesis or isolation can be dissolved in a suitable solvent. Suitable solvents are in particular aqueous solutions which contain a specific proportion of an organic solvent such as, for example, DMSO (dimethylsulfoxide).

Conducting a strain of the yeast with a compound for identifying a compound in accordance with an invention mentioned above is done in particular in automated laboratory systems provided therefor. Such systems may comprise specifically prepared chambers with depressions, or microtiter plates, Eppendorf tubes or laboratory glassware. Automated laboratory systems are usually designed for high throughput rates. A method such as the one mentioned above, carried out with the aid of an automated laboratory system, is therefore also referred to as HTS (High Throughput Screening).

Seq ID No. 1 discloses a polynucleotide sequence comprising the coding region of the GLUT4V85M protein. Seq ID No. 2 discloses the amino acid sequence of the GLUT4V85M protein. Seq ID No. 3 discloses the polynucleotide sequence of the p4H7GLUT4V85M vector.

EXAMPLES

Use of Yeast Strains

All of the yeast strains described herein were derived from strain CEN-PK2-1C (MATa leu2-3, 112 ura3-52 trp1-289 his3-Δ1MAL2-8$^c$ SUC2). The preparation of a yeast strain having deletions in the hexose transporter genes (HXT) has been described by Wieczorke et al., FEBS Lett. 464, 123-128 (1999): EBY-18ga (MATa Δhxt1-17 Δgal2 Δagt1 Δstl1 leu2-3, 112 ura3-52 trp1-289 his3-Δ1 MAL2-8$^c$ SUC2), EBY.VW4000 (MATa Δhxt1-17 Δgal2 Δagt1 Δmph2 Δmph3 Δstl1 leu2-3, 112 ura3-52 trp1-289 his3-Δ1 MAL2-8$^c$ SUC2). The media were based on 1% yeast extract and 2% peptone (YP), while the minimal media were composed of 0.67% Difco yeast nitrogen base without amino acids (YNB) and contained additives required for auxotrophy and different carbon sources. The yeast cells were grown under aerobic conditions at 30° C. on a rotary shaker or on agar plates. Cell growth was monitored by measuring the optical density at 600 nm (OD$_{600}$) or by determining the diameter of yeast colonies.

Determination of Glucose Uptake

Glucose transport was measured as uptake of D-[U-$^{14}$C]-glucoses (Amersham) and the kinetic parameters were determined from Eadie-Hofstee plots. The cells were removed by centrifugation, washed with phosphate-buffer and resuspended in phosphate buffer at a concentration of 60 mg (wet weight) per ml. Glucose uptake was determined for glucose concentrations between 0.2 and 100 mM, and the specific activity of the substrate was between 0.1 and 55.5 kBq µmol$^-$$_1$. The cells and the glucose solutions were preincubated at 30° C. for 5 minutes. Glucose uptake was started by adding radioactive glucose to the cells. After incubation for 5 seconds, 10 ml of ice-cold stop buffer (0.1 M KiPO$_4$, pH 6.5, 500 mM glucose) were added and the cells were removed quickly by filtering on glass fiber filters (Ø=24 mm, Whatman). The filters were quickly washed three times with ice-cold buffer and the radioactivity incorporated was measured using a liquid scintillation counter. An addition by cytochalasin B (final concentration 20 µM, dissolved in ethanol) was measured in a 15-second uptake assay with 50 mM or 100 mM radioactive glucose, after the cells had been incubated in the presence of the inhibitor or of only the solvent for 15 minutes.

A novel heterologous expression system for glucose transporters from mammalian cells has been developed. The system is based on an S. cerevisiae strain from which all endogenous glucose transporters have been removed destroying the encoding genes. Said strain is no longer able to take up glucose via the plasma membrane and to grow with glucose as sole carbon source. In order to integrate the heterologous glucose transporters of humans or of other mammals, GLUT1 and GLUT4 in an active form into the yeast plasma membrane, additional mutations had to be introduced into the yeast strain. GLUT1 is active only in an fgy1-1 mutant strain and GLUT4 only in fgy1-1 fgy4-X double mutants. The FGY1 gene has been cloned. It is the S. cerevisiae ORF YMR212c. With respect to the function, the results indicate that either Fgy1 or a product generated by Fgy1 inhibits the activity of human glucose transporters or is involved in fusing the GLUT-transporting vesicles to the plasma membrane.

In contrast to GLUT1 and similarly to mammalian cells, a large proportion of the GLUT4 proteins in the yeast is located in intracellular structures. A total of nine recessive mutants were isolated (fgy4-1 to fgy4-9) in which GLUT4 is now directed further to the plasma membrane and, in the case of a concomitant fgy1-1 mutation, becomes active there.

The insertion gene bank described by Bruns et al. (Genes Dev. 1994; 8: 1087-105) was used for complementation analysis. The hxt fgy1-1 strain was transformed first with a GLUT4 plasmid and then with the mobilized insertion gene bank. This was followed by screening for transformants which were able to grow on glucose medium. It turned out that in one of the mutants studied the ERG4 gene had been destroyed. ERG4 codes for an enzyme (oxidoreductase) of ergosterol biosynthesis. This enzyme, sterol C-24(28)-reductase catalyzes the last step of ergosterolbiosynthesis and converts ergosta-5,7,22,24,(28)-tetraenol to the final product ergosterol. The Erg4 protein presently contains eight transmembrane domains and is located in the endoplasmic reticulum. An erg4 mutant is viable, since incorporation of the ergosterol precursors into the yeast membranes compensates for the loss of ergosterol.

The inhibiting influence of Erg4 on GLUT4 functionality was confirmed by specific deletion of erg4 in the hxt fgy1-1 strain. The resulting strain (hxt fgy1-1 Δerg4) was referred to as SDY022.

Protein interaction assays with the aid of the split-ubiquitin system showed that human GLUT4 directly interacts with yeast Erg4. It can therefore be assumed that the yeast Erg4 protein in the endoplasmic reticulum either directly prevents further translocation of GLUT4 or modifies GLUT4 in some way which is important for translocation and/or function.

Likewise, it was shown that deletion of ERG4 in the hxt null strain alone, i.e. despite functional FGY1, activates GLUT1, but not GLUT4. The results of the growth assay are summarized in Table 1.

In order to rule out that Ergosterol itself exerts a negative influence on GLUT4, growth assays were carried out on agar plates containing Ergosterol under aerobic conditions. Any yeast strains transformed with GLUT4 were unable to grow under these conditions (Table 2). The GLUT1 transformants in the hxt fgy1-1 strain showed, in contrast to aerobic growth, no growth on glucose under anaerobic conditions. GLUT1 transformants were able to grow only after deletion of ERG4.

The exchange of Val85 for Met by in vitro mutagenesis rendered GLUT4 independent of the fgy1-1 mutation and resulted in GLUT4V85M being functional even in an hxt erg4 strain.

This observation indicates that Fgy1 acts directly or indirectly on this position which is located within the second transmembrane helix of GLUT transporters.

Table 3 displays the descriptions of the yeast strains deposited in connection with the present patent application with the Deutsche Sammlung von Mikroorganismen and Zellkulturen (DSMZ)-Mascheroder Weg 1b 38124 Brunswick, Germany.

TABLE 1

Growth of GLUT1 and GLUT4 transformants on glucose medium.

| Genotype | 1% Glucose | | 1% Glucose | |
|---|---|---|---|---|
| Δhxt fgy1-1 | GLUT4 | − | GLUT1 | ++ |
| Δhxt fgy1-1 Δerg4 | GLUT4 | ++ | GLUT1 | ++ |
| Δhxt fgy1-1 Δerg4 | Vector | − | Vector | − |
| Δhxt fgy1-1 Δerg5 | GLUT4 | − | GLUT1 | ++ |
| Δhxt fgy1-1 Δerg4 Δerg5 | GLUT4 | + | GLUT1 | ++ |
| Δhxt Δerg4 | GLUT4 | − | GLUT1 | + |
| Δhxt Δerg5 | GLUT4 | − | GLUT1 | − |

TABLE 2

Growth of GLUT1 and GLUT4 transformants on glucose medium with or without ergosterol under anaerobic conditions

| Genotype | | 1% Glucose | 1% Glucose + 33 mg/l Ergosterol |
|---|---|---|---|
| Δhxt fgy1-1 | GLUT1 | − | − |
| | GLUT4 | − | − |
| Δhxt fgy1-1 Δerg4 | GLUT1 | − | ++ |
| | GLUT4 | − | − |
| Δhxt fgy1-1 Δerg5 | GLUT1 | − | − |
| | GLUT4 | − | − |
| Δhxt fgy1-1 Δerg4 Δerg5 | GLUT1 | − | ++ |
| | GLUT4 | − | − |
| Δhxt Δerg4 | GLUT1 | − | (+) |
| | GLUT4 | − | − |
| Δhxt Δerg5 | GLUT1 | − | − |
| | GLUT4 | − | − |

TABLE 3

Features of the deposited yeast strains (Saccharomyces cerevisiae)

| Number of deposit with the DSMZ | Genotype | Phenotype | Plasmid |
|---|---|---|---|
| DSM 15187 | MATa Δhxt1-17 Δgal2 Δagt1 Δstl1 Δmph2 Δmph3 Δerg4 leu2-3, 112 ura3-52 trp1-289 his3-Δ1 MAL2-8ᶜ SUC2 | Strain growth with 1% maltose as carbon source; auxotrophic for glucose, leucine, tryptophan, histidine and uracil | — |
| DSM 15184 | MATa Δhxt1-17 Δgal2 Δagt1 Δstl1 Δerg4 fgy1-1 leu2-3, 112 ura3-52 trp1-289 his3-Δ1 MAL2-8ᶜ SUC2 | Strain growth with 1% maltose as carbon source; auxotrophic for glucose, leucine, tryptophan, histidine and uracil | — |
| DSM 15185 | MATa Δhxt1-17 Δgal2 Δagt1 Δstl1 Δmph2 Δmph3 Δerg4 leu2-3, 112 ura3-52 trp1-289 his3-Δ1 MAL2-8ᶜ SUC2 | Strain growth with 1% maltose as carbon source; auxotrophic for glucose, leucine, tryptophan and histidine | p4H7GLUT4V85M (Selection marker URA3), = Seq ID No. 3 |
| DSM 15186 | MATa Δhxt1-17 Δgal2 Δagt1 Δstl1 Δerg4 fgy1-1 leu2-3, 112 ura3-52 trp1-289 his3-Δ1 MAL2-8ᶜ SUC2 | Strain growth with 1% maltose as carbon source; auxotrophic for glucose, leucine, tryptophan and histidine | p4H7GLUT4V85M (Selection marker URA3) = Seq ID No. 3 |
| DSM 15188 | MATa Δhxt1-17 Δgal2 Δagt1 Δstl1 Δmph2 Δmph3 leu2-3, 112 ura3-52 trp1-289 his3-Δ1 | Strain growth with 1% maltose as carbon source; auxotrophic for | p4H7GLUT4V85M (Selection marker URA3) = Seq ID No. 3 |

TABLE 3-continued

Features of the deposited yeast strains (*Saccharomyces cerevisiae*)

| Number of deposit with the DSMZ | Genotype | Phenotype | Plasmid |
|---|---|---|---|
| | MAL2-8$^c$ SUC2 | glucose, leucine, tryptophan and histidine | |

Basic medium: 0.67% Yeast Nitrogen Base without amino acids (Difco); pH 6.2. Auxotrophy supplementation: Leucine (0.44 mM), tryptophan (0.19 mM), histidine (0.25 mM9, uracil (0.44 mM). Maltose may be between 1-2%.

The invention claimed is:

1. An engineered strain of *Saccharomyces cerevisiae*
   (a) which can no longer grow on substrates with hexoses as the only carbon source,
   (b) which lacks a functional protein expressed from *Saccharomyces cerevisiae* open reading frame YMR212c (Fgy1) protein, and
   (c) which further lacks a functional sterol C-24(28)-reductase (Erg4) protein, whose ability of growing on a substrate with a hexose as the only carbon source is restored when a glucose transporter type 4 (GLUT4) gene is expressed in this strain, wherein the GLUT4 gene encodes an amino acid sequence comprising SEQ ID NO:2, wherein the methionine residue of position 85 is a valine residue.

2. The strain of claim 1, wherein said GLUT4 gene restores said strain's ability to grow on a substrate with a hexose as the only carbon source.

3. The strain of claim 2, wherein said GLUT4 gene is a recombinant GLUT4 gene which is under the functional control of a promoter which can be expressed in yeast.

* * * * *